United States Patent
Weber et al.

(10) Patent No.: US 11,627,943 B2
(45) Date of Patent: Apr. 18, 2023

(54) ULTRASOUND IMAGING SYSTEM AND METHOD FOR DERIVING DEPTH AND IDENTIFYING ANATOMICAL FEATURES ASSOCIATED WITH USER IDENTIFIED POINT OR REGION

(71) Applicant: KONINKLIJKE PHILIPS N.V., Eindhoven (NL)

(72) Inventors: Frank Michael Weber, Hamburg (DE); Tobias Wissel, Lübeck (DE); Arne Ewald, Hamburg (DE); Alexander Schmidt-Richberg, Hamburg (DE); Jochen Peters, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/755,822

(22) PCT Filed: Oct. 8, 2018

(86) PCT No.: PCT/EP2018/077259
§ 371 (c)(1),
(2) Date: Apr. 13, 2020

(87) PCT Pub. No.: WO2019/076659
PCT Pub. Date: Apr. 25, 2019

(65) Prior Publication Data
US 2020/0330076 A1     Oct. 22, 2020

(30) Foreign Application Priority Data

Oct. 16, 2017   (EP) .................................. 17196608

(51) Int. Cl.
*A61B 8/08*    (2006.01)
*A61B 8/14*    (2006.01)
*A61B 8/00*    (2006.01)

(52) U.S. Cl.
CPC .............. *A61B 8/5207* (2013.01); *A61B 8/14* (2013.01); *A61B 8/463* (2013.01); *A61B 8/469* (2013.01); *A61B 8/54* (2013.01)

(58) Field of Classification Search
CPC ....... A61B 8/469; A61B 8/463; A61B 8/5207; A61B 8/14; A61B 8/54; A61B 8/465; A61B 8/467; A61B 5/7264
See application file for complete search history.

(56) References Cited

U.S. PATENT DOCUMENTS 6,544,179 B1    4/2003  Schmiesing et al.
9,101,327 B2 *  8/2015  Ho ........................ G01S 15/894
(Continued)

FOREIGN PATENT DOCUMENTS

EP      2702947 A1     3/2014
JP      2009101000 A   5/2009
(Continued)

OTHER PUBLICATIONS

International Search Report and Written Opinion for International Application No. PCT/EP2018/077259, filed Oct. 8, 2018, 13 pages.
(Continued)

*Primary Examiner* — Joel Lamprecht
*Assistant Examiner* — Nyrobi Celestine (57) ABSTRACT

An ultrasound imaging system comprises a display for displaying a received ultrasound image. A user interface is provided for receiving user commands for controlling the ultrasound imaging process, and it receives a user input which identifies a point or region of the displayed ultrasound image. An image depth is determined which is associated with the identified point or region and the imaging process is controlled to tailor the imaging to the identified point or region.

20 Claims, 2 Drawing Sheets

(56) References Cited

U.S. PATENT DOCUMENTS

| | | | |
|---|---|---|---|
| 2006/0058674 A1* | 3/2006 | Olstad | A61B 8/0883 600/450 |
| 2007/0055153 A1 | 3/2007 | Simopoulos et al. | |
| 2008/0072151 A1 | 3/2008 | Song et al. | |
| 2010/0049046 A1 | 2/2010 | Pfeiffer et al. | |
| 2014/0046185 A1* | 2/2014 | Mo | A61B 8/467 600/443 |
| 2014/0098049 A1 | 4/2014 | Koch et al. | |
| 2014/0358006 A1 | 12/2014 | Snyder et al. | |
| 2015/0351726 A1* | 12/2015 | Menon | A61B 8/469 600/443 |
| 2015/0366534 A1 | 12/2015 | Nair et al. | |
| 2015/0375013 A1* | 12/2015 | Lachaine | A61N 5/1067 600/439 |
| 2016/0120508 A1* | 5/2016 | Kim | A61B 8/465 600/443 |
| 2016/0287214 A1* | 10/2016 | Ralovich | A61B 8/5215 |
| 2016/0361043 A1* | 12/2016 | Kim | A61B 8/0891 |
| 2017/0238907 A1 | 8/2017 | Kommu Chs | |
| 2018/0220995 A1* | 8/2018 | Pelissier | A61B 8/5207 |
| 2019/0200963 A1* | 7/2019 | Matsumoto | A61B 8/463 |
| 2020/0151872 A1* | 5/2020 | Ma | A61B 8/085 |

FOREIGN PATENT DOCUMENTS

| | | |
|---|---|---|
| WO | 2005059586 A1 | 6/2005 |
| WO | 2016092403 A1 | 6/2016 |
| WO | 2017068892 A1 | 4/2017 |

OTHER PUBLICATIONS

Ecabert, et al., "Automatic Model-Based Segmentation of the Heart in CT Images", Medical Imaging, IEEE Transactions on, 2008, 27, pp. 1189-1201. (Abstract).

* cited by examiner

ULTRASOUND IMAGING SYSTEM AND METHOD FOR DERIVING DEPTH AND IDENTIFYING ANATOMICAL FEATURES ASSOCIATED WITH USER IDENTIFIED POINT OR REGION

RELATED APPLICATIONS

This application is the U.S. National Phase application under 35 U.S.C. § 371 of International Application No. PCT/EP2018/077259, filed on Oct. 8, 2018, which claims the benefit of and priority to European Application No. 17196608.8, Oct. 16, 2017. These applications are incorporated by reference herein.

FIELD OF THE INVENTION

This invention relates to medical diagnostic imaging systems and, in particular, to ultrasound diagnostic imaging systems with user control of image settings.

BACKGROUND OF THE INVENTION

Ultrasonic diagnostic imaging applications can differ widely in the imaging conditions encountered. When imaging the fetal heart for instance a high frame rate of display is required to accurately image the detail of a rapidly beating heart. In other applications such as the diagnosis of tumors in the liver, a high frame rate is not necessary but a high image quality (resolution) is generally preferred. In some cases the pathology being diagnosed may be deep within the patient's body. In other cases the pathology may be just beneath the skin. These widely differing conditions mean that the sonographer frequently has to change a wide variety of settings on the ultrasound system in order to acquire the best images for a given examination.

Typically, the image settings are adjusted on the imaging console before the first image is acquired. Once the first image is displayed, the parameters are re-adjusted until the operator is satisfied.

The controls occupy space on either the display unit or on a physical control unit of the system. Also, the feedback mechanism is indirect, requiring an iterative adjustment process. For example, changing the frequency from high (resolution, "Res") to medium (general "Gen") may already have the desired effect on imaging depth, or if not, the frequency has to be changed again to low (penetration, "Pen"). As another example, adjusting the time-gain control changes brightness at a certain image depth, but the user may need to try several control sliders to adjust the desired depth.

This may make it difficult especially for inexperienced users to directly find the correct setting, which is why assistance in adjusting such parameters is of interest.

WO 2005/059586 for example discloses the automatic determination of dynamic acquisition parameters. In particular, two of the most frequently used user settings, the Resolution/Speed ("res/speed") control and the Pen/Gen/Res control, are automated. The Res/Speed control adjusts the trade-off between image quality (resolution) and frame rate (speed) by varying imaging parameters such as image line density, multiline order, and number of focal zones. The Pen/Gen/Res control adjusts the trade-off between image resolution and the depth of penetration of ultrasound through control of imaging parameters such as the transmit and receive frequencies. In response to a sensed image motion and/or noise, the relevant image parameters are automatically varied to obtain images which are a sensible balance of these competing factors.

This easy adjustment is attractive to a user, but the user may still want control over which adjustments are made and how they affect the image.

There remains a need for simplified user controls but which still give ultimate control to the user for controlling the ultrasonic imaging to give desired tissue penetration, imaging frame rate, and image resolution.

Document EP 2 702 947 discloses an ultrasound imaging apparatus configured with a touch screen display and computer aided measurement and/or diagnosis capability.

Document US 2014/098049 discloses a system for receiving touch-based input from an operator of an imaging device.

SUMMARY OF THE INVENTION

The invention is defined by the claims.

According to examples in accordance with an aspect of the invention, there is provided an ultrasound imaging system, comprising:

an ultrasound probe for generating ultrasound signals and receiving reflected echo signals;

a processing system for controlling the generation of the ultrasound signals and processing of the received reflected echo signals;

a display for displaying a received ultrasound image; and a user interface for receiving user commands for controlling the generation of the ultrasound signals and/or processing of the received reflected echo signals, wherein the user interface is adapted to receive a user input which identifies a point or region of a displayed ultrasound image, and wherein the processing system is adapted to derive an anatomical feature identification and/or an image depth associated with the identified point or region and control the generation of the ultrasound signals and processing of the received reflected echo signals to adapt them to the identified point or region.

This system enables a user to select a point or region of an image, and the ultrasound imaging parameters may then be controlled automatically to optimize the imaging for that particular region. The parameters controlled relate to the diagnostic imaging procedure (i.e. the acquisition, processing and display of image data). Examples of parameters that may be controlled are the focal zone, the frequency, the time gain compensation settings, overall imaging gain, frame rate etc. These parameters are all for controlling the eventual display such that it is optimized for the display of a particular anatomical area or feature of interest, rather than a generic display setting (such as a generic brightness or contrast setting).

In a simplest implementation, the user identifies the point or region, and a standard parameter optimization is carried out. The depth (from the ultrasound head to the region of tissue) of the identified point or region is for example identified and this enables automated or semi-automated adjustment of the imaging parameters.

In a system in which depth information is derived, the processing system for example may be adapted to adjust the frequency in response to the derived depth. The frequency control is thus used to ensure a minimum amplitude for the echo signal at the particular depth.

The processing system may be adapted to adapt the frequency to maximize the received signal. This may for example make use of closed loop control.

In a system based on anatomical feature recognition, the processing system may be adapted to identify anatomical structures within the image and to identify an anatomical structure at the identified point or region, and to control the generation of the ultrasound signals and/or processing of the received reflected echo signals to adapt them to the identified anatomical structure.

The system may then apply the best imaging parameters for a particular anatomical structure. For example, the identification of the mitral valve, based on a segmentation label, may cause the frame rate to be adjusted. This does not require specific knowledge of the depth for the required frame rate adjustment to be carried out.

The processing system may be adapted to adjust one or more of:
  the frame rate;
  the contrast;
  the gain settings;
  the focal zone.

The frame rate may for example be increased for a moving structure such as the heart, whereas a lower frame rate for a stationary structure may enable higher quality imaging. Contrast control may be used to make a structure, such as a ventricle wall, more easily visible.

Model based segmentation may be used to identify the anatomical structures, although other approaches, such as machine learning, may also be used.

The user interface is for example adapted to receive a further command. This enables the user to have some control over the parameter optimization as well as or instead of a fully automated option.

In a first example, the further command indicates that focal depth adjustment is desired, and the processing system is adapted to adjust the frequency and/or scanning aperture in response to the derived depth. The scanning aperture is also used to influence the focal depth.

Thus, in this case, the user may need to specify that depth adjustment is desired as one of several possible options, instead of a fully automated depth adjustment.

In a second example, the further command indicates that focal zone adjustment is desired, and the processing system is adapted to adjust the width of the beam at the focus and the focus depth in response to the derived depth. This beam width is dependent on the frequency and aperture and determines the resolution at the focus and also at other regions outside the focus.

In a third example, the size of the field of view may be controlled. By adjusting the field of view, a zoom in operation is implemented to the image region of interest.

In a fourth example, the further command indicates that a gain adjustment is desired (e.g. overall imaging gain or depth-dependent time gain compensation), and the processing system is adapted to adjust the gain setting, such as the time gain compensation, in response to the derived depth.

Time gain compensation is used to account for tissue attenuation. By increasing the received signal intensity with depth, the artifacts in the uniformity of a B-mode image intensity are reduced. Different time gain compensation functions may be appropriate for different scan lines, and the user can input when time gain compensation changes are desired, but they can then be altered automatically taking into account the identified point or region.

The user interface may be adapted to receive the further command as one or more of:
  a touch screen pinch command;
  a single click mouse or touch screen command;
  a double click mouse or touch screen command;
  a two finger touch screen interaction;
  a mouse or touch screen slider interaction;
  a selection from a list of options.

Thus, various touch screen or mouse commands may be used to enable the user to input commands beyond the mere identification of the point or region of interest.

The user interface may be adapted to receive the user input which identifies a point or region as one or more of:
  a touch screen point identification;
  a region drawn over a touch screen;
  a single click point identification using a mouse;
  a region drawn using a mouse.

The initial identification of the point of region of interest may be a simple single click function or a simple region drawing function, again using a mouse or touch screen.

The invention also provides an ultrasound imaging method, comprising:
  generating ultrasound signals and receiving and processing reflected echo signals;
  displaying a received ultrasound image; and
  receiving user commands for controlling the generation of the ultrasound signals and/or processing of the received reflected echo signals, wherein the user commands identify a point or region of a displayed ultrasound image,
  wherein the method comprises deriving an anatomical feature identification and/or an image depth associated with the identified point or region and controlling the generation of the ultrasound signals and processing of the received reflected echo signals to adapt them to the identified point or region.

This method provides automated parameter control based on an identified region of an ultrasound image.

The method for example comprises adapting the frequency in response to a derived depth.

The method may comprise identifying anatomical structures within the image and identifying an anatomical structure at the identified point or region, and
  controlling the generation of the ultrasound signals and/or processing of the received reflected echo signals to adapt them to the identified anatomical structure. Model based segmentation may be used to identify the anatomical structures.

In response to the anatomical structure identified, the method may provide adjustment of one or more of:
  the frame rate;
  the contrast;
  the gain settings;
  the focal zone.

Different adjustments may be appropriate for different

The method may comprise receiving a further user command, wherein:
  the further command indicates that focal depth adjustment is desired, and the method comprises adapting the frequency in response to the derived depth; or
  the further command indicates that focal zone adjustment is desired, and the method comprises adjusting the width of the beam at the focus and the focus depth in response to the derived depth; or
  the further command indicates that a field of view adjustment is desired, and the method comprises adjusting the field of view in response to the derived depth; or the further command indicates that time gain compensation adjustment is desired, and the method comprises adapting the time gain compensation in response to the derived depth.

The invention may be implemented at least in part in computer software.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound imaging system which comprises a display for displaying a received ultrasound image. A user interface is provided for receiving user commands for controlling the ultrasound imaging process, and it receives a user input which identifies a point or region of the displayed ultrasound image. An image depth is determined which is associated with the identified point or region and the imaging process is controlled to tailor the imaging to the identified point or region.

Figure 1:
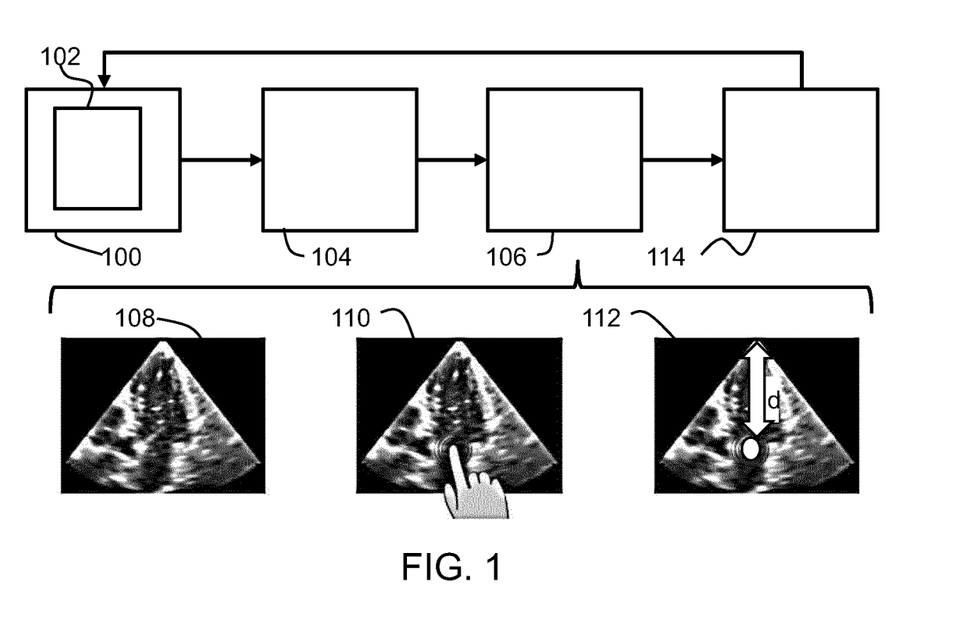
FIG. 1 shows a first example of an ultrasound system in schematic form.

FIG. 1 shows an ultrasound imaging system together with some display outputs to show how the user controls the imaging settings.

The system comprises an ultrasound imaging unit 100, i.e. probe, for generating ultrasound signals and receiving reflected echo signals. The imaging unit 100 includes a processing system 102 for controlling the generation of the ultrasound signals and processing of the received reflected echo signals.

A display 104 is provided for displaying the received ultrasound images and a user interface 106 is provided for receiving user commands for controlling the generation of the ultrasound signals and/or processing of the received reflected echo signals.

The user interface 106 may comprise a touch screen of the display 104 and hence it may be part of the display rather than a separate unit as schematically shown in FIG. 1. The user interface 106 allows the user to input commands in response to the displayed image. The user interface 106 may additionally or alternatively comprise a mouse which is used to control a pointer on the display such that the pointer may be moved to a desired part of the displayed image. There may of course be other user input controls such as a keyboard, voice recognition etc.

The user interface 106 receives a user input which identifies a point or region of a displayed ultrasound image.

Pane 108 shows an ultrasound image. Pane 110 shows a user selecting a point in the image by touching the touch screen display. A single point may be identified by touching the screen or a region may be identified by drawing a closed shape. Pane 112 shows that a distance d from the imaging unit (ultrasound probe) 100 to the identified point of the image is derived. This distance d is then used to provide automated or semi-automated control the generation of the ultrasound signals and/or processing of the received reflected echo signals to adapt them to the identified point or region. The control involves selecting suitable parameters relating to the diagnostic imaging procedure. Examples of parameters that may be controlled are the focal zone, the frequency, the aperture (i.e. the active size of matrix array), the angular extent of the field of view, the imaging depth, the number of scan lines to be acquired within the field of view, settings for gain and dynamic range (e.g. overall gain, time gain compensation, dynamic range during RF conversion and image display), scanning power, scan angle (transducer rotation, e.g. for transesophageal ultrasound probes), use of harmonic frequencies, smoothing/time averaging, frame rate etc.

In a simplest implementation, the user identifies the point or region, and a standard parameter optimization is carried out.

A feedback unit 114 relates the location of the interaction with the image to the acquisition geometry. The feedback unit 114 knows the position of the transducer in the image (and for a 3D dataset also the displayed cut-plane), so that the tissue depth of the identified point or region can be calculated. Using a rule-of-thumb for attenuation such as 1 dB/cmMHz, the frequency can then be adjusted to ensure at least a minimum amplitude for the returning signal.

The processing system 102 can then relate the user input command to the acquisition parameters and alter the acquisition parameters of the imaging system. Furthermore, the feedback unit 114 and imaging unit 100 can be connected in a closed-loop to check that the parameter changes have the desired effect.

The system thus provides setting adjustments by allowing the user to interact directly with the image. For example, after taking a first image, the user may click into the image at a certain depth (which may be the maximum depth he/she wants to image with a certain resolution), and the system may then automatically select the best matching frequency and focus setting for this depth.

The user input may have multiple options, such as a single-click, a double-click, a one-finger touch interaction or a two-finger touch interaction, wherein each type of interaction has a different meaning (such as adjusting frequency for a certain point or a focal zone for a certain point).

Specific multi-finger gestures may also be recognized, such as a two-finger zoom ("pinch gesture") to adjust the image depth or the field of view angle.

For a given type of interaction, menu options may also be presented. For example a menu may be used to assign the interaction with a certain meaning, such as selecting a parameter from a list (e.g. "frequency", "focal zone" etc. . . . ).

Thus, it can be seen that the user interface in this way can allow further commands to be received in addition to the location identification.

Some specific examples will now be presented of how multiple commands (location and other commands) may be used.

Time-gain-compensation (TGC) can be adjusted by clicking and sliding at a certain distance from the transducer. As the distance from the transducer is known, it can be calculated from the depth which TGC setting needs to be changed. The sliding motion determines how much the TGC for the specified depth should be increased/decreased.

The user may also be allowed to explicitly specify that at given locations, a specified amount of signal would be expected (e.g. in the ventricle wall or in the mitral valve region). For example, the user could assign an anatomical region to the point from a drop-down-menu, such as "LV Myocardium". The system could then adjust the frequency to maximize the signal, for example, using closed-loop adjustment between the imaging unit 100 and the feedback unit 114, i.e. adjusting the frequency until the signal is satisfactory.

A further command in addition to location may be used to indicate that focal depth adjustment is desired, and the processing system then adjusts the frequency and/or scanning aperture in response to the derived depth.

A further command may indicate that focal zone adjustment is desired, and the processing system then adjusts the width of the beam at the focus and the focus depth in response to the derived depth. The beam width is for example controlled based on the frequency and aperture, and it determines the resolution at the focus and also at other regions outside the focus. The focus depth is the distance from the transducer to the focus point at which the beam width is minimal.

A further command may indicate that a field of view adjustment is desired, and the processing system is adapted to adjust the field of view in response to the derived depth. By adjusting the field of view to a region of interest, a zoom in operation is implemented.

As outlined above, many other imaging parameters may be adjusted. There may be some parameters which are adjusted automatically in response to an identified anatomical feature or depth, and other parameters which are adjusted based on user instructions.

Figure 2:
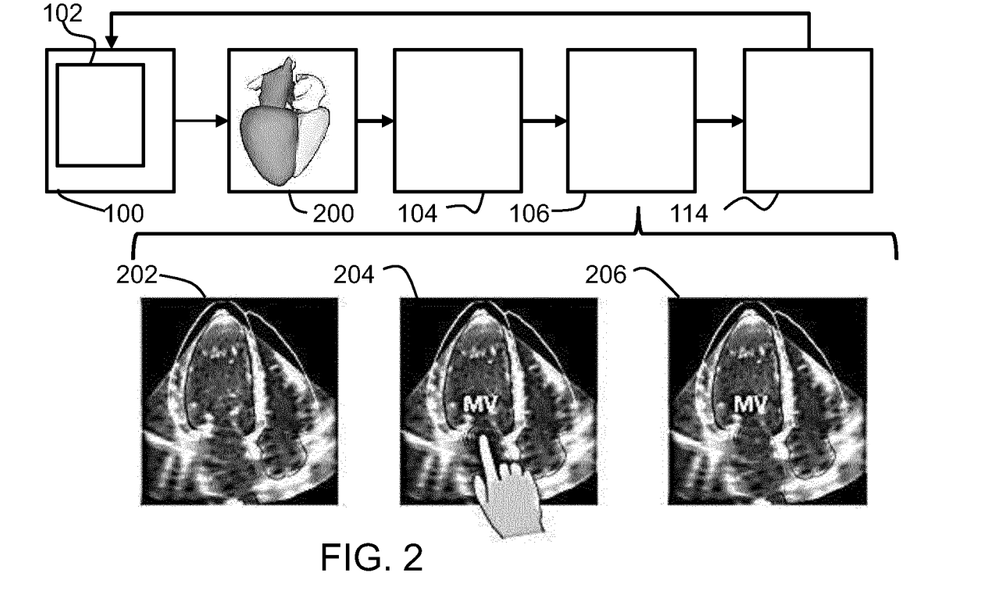
FIG. 2 shows a second example of an ultrasound system in schematic form.

FIG. 2 shows a modification to the system of FIG. 1 to identify anatomical structures within the displayed image and to identify an anatomical structure at the identified point or region. The system may then apply the best imaging parameters for a particular anatomical structure.

For certain adjustments, it may not only be helpful to interact with the displayed image, but also to consider the anatomical context. For example, contrast enhancement of the boundary between LV myocardium and blood pool is difficult if the location of the boundary in the images is not known. Also, for automatic frame rate adjustment based on motion of the imaged anatomical structure, it may be important if a certain motion is relevant for the acquisition or not.

The same references are used as in FIG. 1 for the same components.

The system has an additional segmentation unit 200. Model-based segmentation, neural networks or deep learning may be used for anatomical segmentation. Pane 202 shows an image showing segmentations. Pane 204 shows the user selection of a point or region. The system then determines the anatomical structure which has been selected, and provides image parameter modification to generate an improved image shown as pane 206.

Different anatomical structures for example make different frame rate, contrast or focal zone appropriate. Selection of the optimal imaging parameters can be performed using a database or directly from image/anatomy properties.

The display 104 shows the anatomical context, for example as mesh overlay over the image. The anatomical context is provided by the adapted model of the model-based segmentation. For example, if the model consists of a triangular mesh, each triangle may have assigned anatomical labels. This way, the user does not have to assign an anatomical label him or herself.

By way of example, if the user selects a heart valve which is known to move fast, a higher frame rate is chosen. If the user in the same field of view selects the heart chamber, a lower frame rate but higher spatial resolution is selected. This can be done based on stored knowledge about typical frame rates required, or based on motion detection.

In another example, the user can select the ventricular wall, and the system can optimize the contrast between the wall and surrounding regions. To this end, several frequency, focus and time-gain control settings can be tested. For each setting, an objective function is calculated, such as the difference between the mean intensity inside the wall region and inside the blood region. The setting that maximizes (or for different objective functions minimizes) the function is used. An alternative objective function would be the more local intensity difference across a triangular surface, for example, the surface separating the wall and blood region. For image depths at which this is lower, the time-gain-compensation setting could be adjusted.

As another example, a structure may be selected in a first acquisition, and for following acquisitions from different probe locations, the settings are automatically adjusted to best image that structure. For example, for a mid-esophageal image of a ventricular septal defect, the defect is quite far away from the transducer/probe. If the defect is selected in the first acquisition and the probe is moved further down the esophagus for the acquisition, a higher frequency is automatically chosen the closer the probe is located to the defect. This always provides an optimized relation between spatial resolution and signal strength at the region of interest.

If a structure is selected which is currently only partly in the image, the field of view extent (lateral and depth) may be adjusted such that the complete structure is inside the image, or if that is not possible, the largest possible part is visible. This is feasible because from the adapted model, the rough extent of the structure can be estimated.

Thus, it can be seen that there are different possible levels of automated or semi-automated control, but they all rely at least on knowledge of the region of an image which has been selected and the corresponding depth of that anatomical area from the transducer (whether or not the anatomical area is identified).

Figure 3:
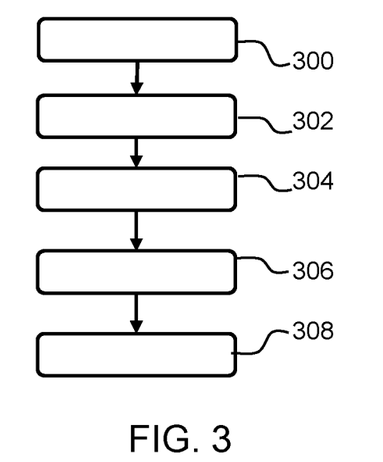
FIG. 3 shows an ultrasound imaging method.

FIG. 3 shows an ultrasound imaging method, comprising, in step 300, generating ultrasound signals and receiving and processing reflected echo signals.

In step 302, a received ultrasound image is displayed and in step 304, user commands for controlling the generation of the ultrasound signals and/or processing of the received reflected echo signals are received. These user commands identify a point or region of a displayed ultrasound image.

The user input identifies a point or region as a touch screen point identification, a region drawn over a touch screen, a single click point identification using a mouse or a region drawn using a mouse.

The method comprises step 306 of deriving an anatomical feature identification and/or an image depth associated with the identified point or region. In step 308, the generation of the ultrasound signals and/or processing of the received reflected echo signals are controlled to adapt them to the identified point or region.

This may take account of additional user input, such as a touch screen pinch command, a single click mouse or touch screen command, a double click mouse or touch screen command, a two finger touch screen interaction, a mouse or touch screen slider interaction or a selection from a list of options.

Figure 4:
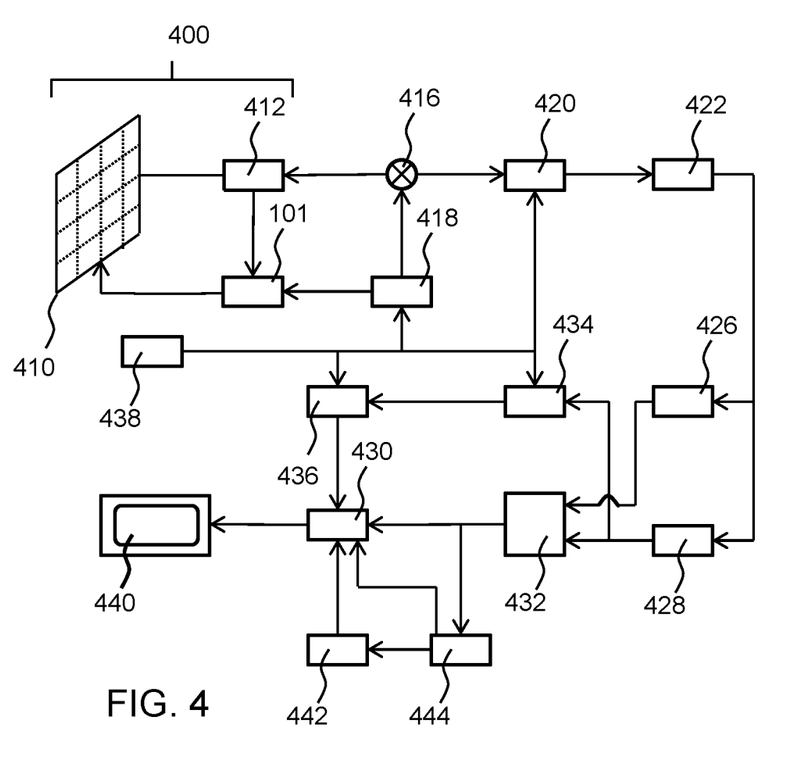
FIG. 4 shows in more detail a known component structure of an ultrasound imaging system.

The general operation of the ultrasound system including its drive electronics can be standard and is not described in detail. However, for completeness. FIG. 4 shows an ultrasonic diagnostic imaging system with an array transducer probe according to an example in block diagram form.

In FIG. 4 an ultrasound system 400 is shown which comprises capacitive micromachined ultrasound transducer (CMUT) cells for transmitting ultrasonic waves and receiving echo information. The transducer array 410 of the system 400 may be a one- or a two-dimensional array of transducer elements capable of scanning in a 2D plane or in three dimensions for 3D imaging.

The transducer array 410 is coupled to a micro-beamformer 412 which controls transmission and reception of signals by the CMUT array cells. Micro-beamformers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The micro-beamformer 412 is coupled by the probe cable, e.g. coaxial wire, to a transmit/receive (T/R) switch 416 which switches between transmission and reception modes and protects the main beam former 420 from high energy transmit signals when a micro-beamformer is not present or used and the transducer array 410 is operated directly by the main beam former 420. The transmission of ultrasonic beams from the transducer array 410 under control of the micro-beamformer 412 is directed by a transducer controller 418 coupled to the micro-beamformer by the T/R switch 416 and the main beam former 420, which receives input from the user's operation of the user control panel or user interface 438. One of the functions controlled by the transducer controller 418 is the direction in which beams are steered and focused. Beams may be steered straight ahead from (orthogonal to) the transducer array 410, or at different angles for a wider field of view. The transducer controller 418 may be coupled to control the aforementioned voltage source 101 for the transducer array 410. For instance, the voltage source 101 sets the DC and AC bias voltage(s) that are applied to the CMUT cells of a transducer array 410, e.g. to generate the ultrasonic RF pulses in transmission mode as explained above.

The partially beam-formed signals produced by the micro-beamformer 412 are forwarded to the main beam former 420 where partially beam-formed signals from individual patches of transducer elements are combined into a fully beam-formed signal. For example, the main beam former 420 may have 128 channels, each of which receives a partially beam-formed signal from a patch of dozens or hundreds of CMUT transducer cells. In this way the signals received by thousands of transducer elements of a transducer array 410 can contribute efficiently to a single beam-formed signal.

The beam-formed signals are coupled to a signal processor 422. The signal processor 422 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 422 optionally may perform additional signal enhancement such as speckle reduction, signal compounding, and noise elimination. The bandpass filter in the signal processor 422 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 426 and optionally to a Doppler processor 428. The B-mode processor 426 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 428, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 432 and a multiplanar reformatter 444. The scan converter 432 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 444 will convert echoes which are received from points in a common plane in a volumetric region of the body into an ultrasonic image of that plane, for instance as described in U.S. Pat. No. 6,443,896 (Detmer). A volume renderer 442 converts the echo signals of a 3D data set into a projected 3D image as viewed from a given reference point as described in U.S. Pat. No. 6,530,885 (Entrekin et al.)

The 2D or 3D images are coupled from the scan converter 432, multiplanar reformatter 444, and volume renderer 442 to an image processor 430 for further enhancement, buffering and temporary storage for display on an image display 440. In addition to being used for imaging, the blood flow values produced by the Doppler processor 428 and tissue structure information produced by the B-mode processor 426 are coupled to a quantification processor 434. The quantification processor 434 produces measures of different flow conditions such as the volume rate of blood flow as well as structural measurements such as the sizes of organs and gestational age. The quantification processor 434 may receive input from the user interface 438, such as the point in the anatomy of an image where a measurement is to be made.

Output data from the quantification processor 434 is coupled to a graphics processor 436 for the reproduction of measurement graphics and values with the image on the display 440. The graphics processor 436 can also generate graphic overlays for display with the ultrasound images. These graphic overlays can contain standard identifying information such as patient name, date and time of the image, imaging parameters, and the like. For these purposes the graphics processor 436 receives input from the user interface 438, such as patient name.

The user interface 438 is also coupled to the transducer controller 418 to control the generation of ultrasound signals from the transducer array 410 and hence the images produced by the transducer array 410 and the ultrasound system. The user interface 438 is also coupled to the multiplanar reformatter 444 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the micro-beamformer 412 and/or the Doppler processor 428 may be omitted, the transducer array 410 may not have 3D imaging capabilities and so on. Other variations will be apparent to the skilled person.

The invention is of interest for general imaging applications or indeed for guided vascular access such as guidewire, catheter or needle tip tracking.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound imaging system, comprising:
   an ultrasound probe for generating ultrasound signals and receiving reflected echo signals;
   a processing system for controlling the generation of the ultrasound signals and processing of the received reflected echo signals;
   a display for displaying a received ultrasound image based on the received reflected echo signals; and
   a user interface for receiving user commands from a user for controlling the generation of the ultrasound signals and the processing of the received reflected echo signals,
   wherein the user interface is configured to receive a user input from the user interacting with an ultrasound image displayed on the display,
   wherein the user input identifies a point or region of interest in the displayed ultrasound image, and
   wherein the processing system is configured to
   receive input data from the user interface indicating the identified point or region of interest in the displayed ultrasound image, and
   automatically, in response to the input data:
      derive a depth of the identified point or region of interest relative to the ultrasound probe,
      identify an anatomical feature associated with the identified point or region of interest at the derived depth, and
      adapt the generation of the ultrasound signals and the processing of the received reflected echo signals to the identified point or region of interest based on the derived depth and the identified anatomical feature at the derived depth.

2. The system as claimed in claim 1, wherein the processing system is further configured to adjust at least one of:
   a frame rate;
   a contrast;
   a gain setting; or
   a focal zone.

3. The system as claimed in claim 1, wherein the processing system is configured to adapt the generation of the ultrasound signals by adjusting frequency of the ultrasound signals in response to the derived depth.

4. The system as claimed in claim 1, wherein the processing system is configured to adapt the generation of the ultrasound signals by adjusting frequency of the ultrasound signals to maximize the received reflected echo signals.

5. The system as claimed in claim 1, wherein the processing system is configured to further identify anatomical structures within the displayed ultrasound image, and to further adapt the generation of the ultrasound signals and the processing of the received reflected echo signals to the identified anatomical structures.

6. The system as claimed in claim 1, wherein the user interface is further configured to receive a further user command indicating that focal depth adjustment is desired, and the processing system is further configured to adjust frequency of the ultrasound signals in response to the derived depth.

7. The system as claimed in claim 1, wherein the user interface is further configured to receive further user command as at least one of:
- a touch screen pinch command;
- a single click mouse or touch screen command;
- a double click mouse or touch screen command;
- a two finger touch screen interaction;
- a mouse or touch screen slider interaction; or
- a selection from a list of options.

8. The system as claimed in claim 1, wherein the user interface is further configured to receive the user input as at least one of:
- a touch screen point identification;
- a region drawn over a touch screen;
- a single click point identification using a mouse; or
- a region drawn using a mouse.

9. An ultrasound imaging method, comprising:
- generating ultrasound signals and receiving and processing reflected echo signals;
- displaying a received ultrasound image based on the received reflected echo signals;
- receiving a user input via a user interface from a user interacting with the ultrasound image displayed on the display to identify a point or region of interest in the displayed ultrasound image;
- receiving input data from the user interface indicating the identified point or region of interest in the displayed ultrasound image; and
- automatically, in response to the input data:
  - deriving a depth of the identified point or region of interest;
  - identifying an anatomical feature associated with the identified point or region of interest at the derived depth; and
  - adapting the generation of the ultrasound signals and processing of the received reflected echo signals to the identified point or region of interest based on the derived depth and the identified anatomical feature at the derived depth.

10. The method as claimed in claim 9, wherein adapting the generation of the ultrasound signals comprises adjusting at least one of:
- a frame rate;
- a contrast;
- a gain setting; or
- a focal zone.

11. The method as claimed in claim 9, wherein adapting the generation of the ultrasound signals comprises adapting frequency of the ultrasound signals in response to the derived depth.

12. The method as claimed in claim 9, further comprising:
- identifying anatomical structures within the displayed ultrasound image; and
- further adapting the generation of the ultrasound signals and processing of the received reflected echo signals to the identified anatomical structures.

13. The method as claimed in claim 9, further comprising receiving a further user command indicating that focal depth adjustment is desired, and adjusting frequency of the ultrasound signals in response to the derived depth.

14. The method as claimed in claim 13, wherein receiving the user input comprises as at least one of:
- a touch screen pinch command;
- a single click mouse or touch screen command;
- a double click mouse or touch screen command;
- a two finger touch screen interaction;
- a mouse or touch screen slider interaction; or
- a selection from a list of options.

15. The system as claimed in claim 1, wherein the user interface is further configured to receive a further user command indicating that focal zone adjustment is desired, and the processing system is further configured to adjust a width of a beam of the ultrasound signals at a focus and a focus depth in response to the derived depth.

16. The system as claimed in claim 1, wherein the user interface is further configured to receive a further user command indicating that adjustment of a field of view is desired, and the processing system is further configured to adjust the field of view in response to the derived depth.

17. The system as claimed in claim 1, wherein the user interface is further configured to receive a further user command indicating that adjustment of time gain compensation is desired, and the processing system is further configured to adjust the time gain compensation in response to the derived depth.

18. The method as claimed in claim 9, further comprising receiving a further user command indicating that focal zone adjustment is desired, and adjusting a width of a beam of the ultrasound signals at a focus and a focus depth in response to the derived depth.

19. The method as claimed in claim 9, further comprising receiving a further user command indicating that adjustment of time gain compensation is desired, and adapting the time gain compensation in response to the derived depth.

20. The system of claim 1, wherein the user interface comprises a touchscreen on the display, and wherein the user input comprises a touch on the touchscreen identifying the point of interest or a drawing on the touchscreen identifying the region of interest.

* * * * *